United States Patent [19]

Laemmle et al.

[11] 3,972,948
[45] Aug. 3, 1976

[54] ANHYDROUS CATALYST FOR MANUFACTURE OF GLYCOL ETHERS

[75] Inventors: George Joseph Laemmle, Port Arthur; Kenneth Carol Rightmer, Nederland, both of Tex.

[73] Assignee: Jefferson Chemical Company, Inc., Houston, Tex.

[22] Filed: Nov. 29, 1974

[21] Appl. No.: 528,425

[52] U.S. Cl. .......................... 260/615 R; 260/615 B
[51] Int. Cl.² ................... C07C 41/02; C07C 41/10
[58] Field of Search ...................... 260/615 R, 615 B

[56] References Cited
UNITED STATES PATENTS

| | | | |
|---|---|---|---|
| 2,508,036 | 5/1950 | Kosmin | 260/615 B |
| 2,834,820 | 5/1958 | Bloch | 260/615 B X |
| 2,932,670 | 4/1960 | Blake | 260/615 B |
| 3,346,557 | 10/1967 | Patton et al. | 260/615 B |

*Primary Examiner*—Howard T. Mars
*Attorney, Agent, or Firm*—James L. Bailey; John R. Kirk, Jr.; Lee G. Meyer

[57] ABSTRACT

An improved process for preparing mono- and poly-glycol ethers by mixing and reacting an alkylene oxide and an alcohol in the presence of a catalyst containing alkali or alkaline earth cations at temperatures within the range of about 50° to about 350°C. under pressure of between about 30 to about 3,000 psig is disclosed. An anhydrous high boiling liquid residue, prepared by the concentration of the liquid reaction product effluent residue remaining after desired mono- and poly-glycol ethers have been separated therefrom has been found to be highly useful as the catalyst for the described process. The employment of the anhydrous high boiling liquid residue as a catalyst advantageously results in the production of liquid reaction product effluents containing relatively little, if any, undesirable glycol by-products which are difficult to separate from the desired mono- and poly-glycol ethers. In a continuous process for preparing mono- and poly-glycol ethers, the concentrated anhydrous, high boiling liquid residue of the invention can be recycled for admixture with the alkylene oxide and alcohol reactant feed streams in the reactor used as the catalyst of the reaction.

8 Claims, 1 Drawing Figure

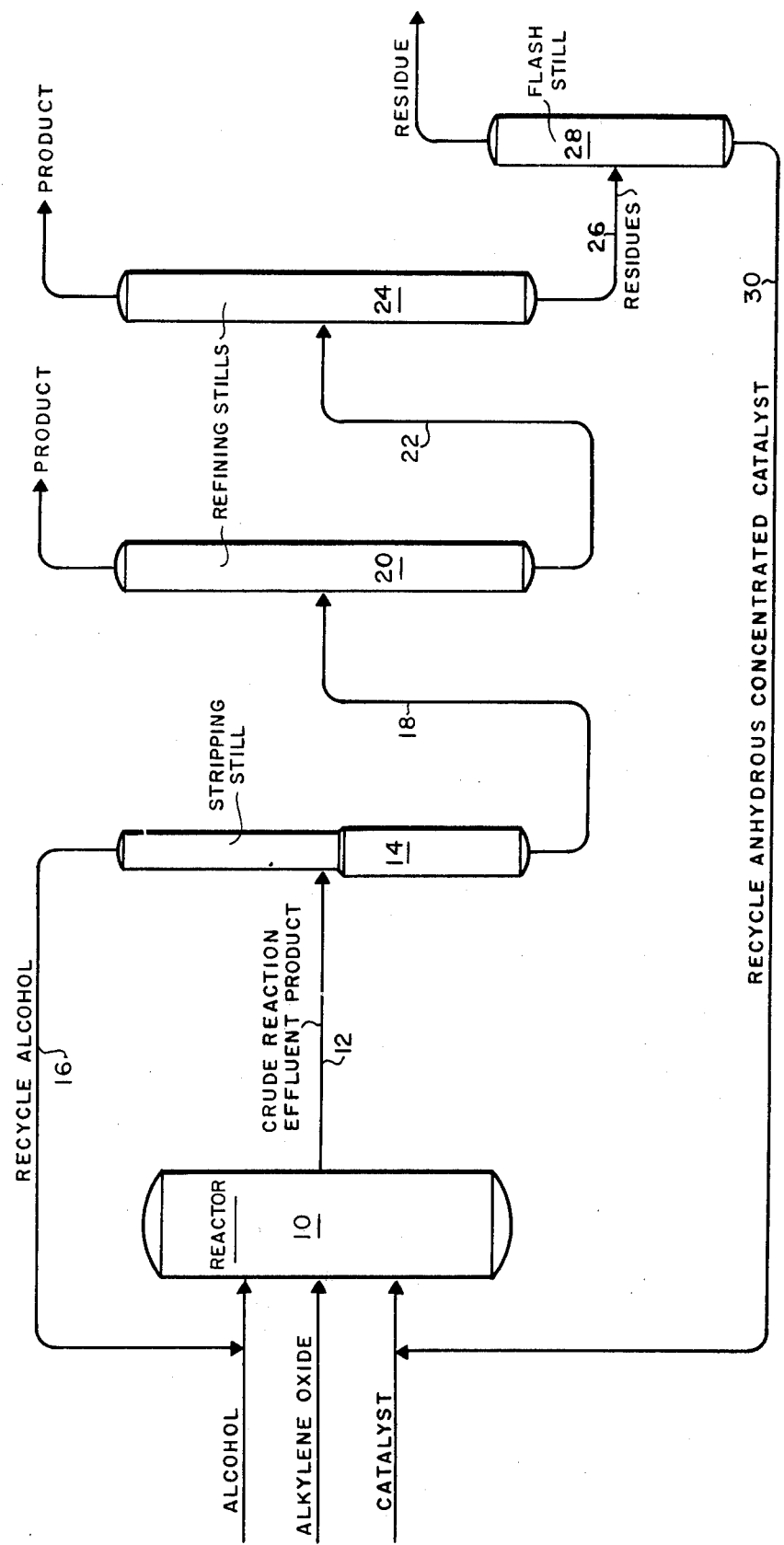

ANHYDROUS CATALYST FOR MANUFACTURE OF GLYCOL ETHERS

DESCRIPTION OF THE PRIOR ART

The production of mono- and poly-glycol ethers by the catalytic reaction of an alkylene oxide and an alcohol in the presence of a catalyst containing alkali or alkaline earth cations is well-known. In accordance with prior art procedures, mono- and poly-glycol ethers are usually prepared by mixing an alcohol, a concentrated aqueous or alcoholic solution of an alkali metal or alkaline earth metal hydroxide and an alkylene oxide, and heating the admixture to about 50° to about 300°C. under pressure between about 30 to about 3,000 psig. The following reactions generally occur:

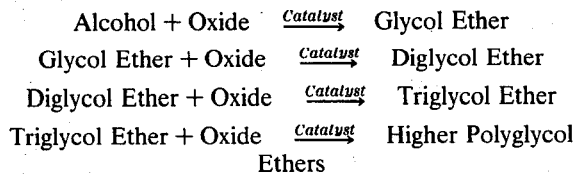

The above reactions occur substantially simultaneously with the distribution of products being determined by the molar ratio of alcohol to oxide employed. This ratio usually ranges from about 0.5 to about 20 moles of alcohol per mole of oxide. As known, the reactant molar ratio can be adjusted to provide a reaction product containing, within certain limits, any desired distribution of mono- and/or poly-glycol ethers.

The liquid reaction product effluent is then purified to separate the desired mono- and poly-glycol ethers and excess unreacted alcohol for reuse therefrom. The liquid residue, higher gylcol ethers, alkali or alkaline earth alcoholates and other reaction by-products is usually discarded or burned as plant fuel. The purification and separation is usually carried out by employing a plurality of distillation or fractionating towers operated at various known conditions for taking the desired products overhead. A typical example is a system employing at least three fractional distillation towers wherein unreacted alcohol is taken overhead from the first tower and the desired glycol ethers are removed overhead from the remaining towers as the liquid product effluent is passed therethrough. Such procedures are usually carried out in a continuous manner through the employment of continuous processing procedures and equipment all well-known in the art.

However, the conventional procedures for the preparation of glycol ethers suffer from the disadvantage of employing aqueous or alcohol solutions of alkali metal or alkaline earth metal hydroxide catalysts. It is well known that alkylene oxides are hydrated in the presence of water to form alkylene glycols. It is extremely difficult to separate the desired mono- and poly-glycol ethers from these by-product alkylene glycols for the respective boiling points are close. The by-product glycols usually appear in the separated desired glycol ether fractions as contaminants. If relatively pure specification product is desired, additional separation treatment is required, which is usually not economically practical.

Several attempts have been made to eliminate or reduce the production of undesirable glycol contaminant by-products. For example, as briefly mentioned hereinbefore, attempts have been made to utilize soluble alkali or alkaline earth alcoholates as the catalyst. As known, these alcoholate catalysts are prepared by first reacting an alcohol with the hydroxide of an alkali metal or alkaline earth metal. However, such reactions inherently produce water as a by-product, which results in glycol formation when used as catalysts. Further attempts have been made to dry the resulting alcoholates, but this has been found to be extremely difficult and economically impractical. Moreover, it has been found that as the molecular weight of the alcohol employed increases, the reaction rate between that alcohol and the alkali or alkaline earth metal decreases with attendant difficulty in catalyst solution preparation.

Accordingly, it is a primary object of the present invention to provide an improvement in the process for preparing mono- and poly-glycol ethers whereby the presence of water is eliminated, thus eliminating the formation of undesirable glycol contaminants.

It is another object of the present invention to provide an improvement in the process for the preparation of mono- and poly-glycol ethers wherein the desired glycol ethers can be readily separated from the reaction product effluent with substantially no glycol contamination.

It is a further object of the invention to provide a utilization for the liquid reaction product effluent residue from a mono- and poly-glycol ether process which is conventionally discarded or employed as a plant fuel.

It is yet another object of the present invention to provide a treatment for the liquid reaction product residue from a mono- and poly-glycol ether process to provide an anhydrous catalyst useful in such processes for the production of such glycol ethers whereby the presence of water and the production of undesirable glycol contaminants are eliminated.

It is yet another object of the invention to provide an improvement in the continuous process for preparing mono- and poly-glycol ether products wherein the liquid reaction product residue from such process is continuously concentrated and recycled for use as the catalyst for the alkylene oxide and alcohol reaction.

SUMMARY OF THE INVENTION

This invention relates to the utilization of an anhydrous high boiling liquid residue containing catalytically active alcoholates of alkali and alkaline earth metals as the catalyst in the process of preparing mono- and poly-glycol ethers. The anhydrous high boiling liquid residue is prepared by concentrating the liquid reaction product effluent residue from the reaction of an alkylene oxide and an alcohol in the presence of a catalyst containing alkali or alkaline earth cations after desired mono- and poly-glycol ethers have been separated therefrom. The utilization of the anhydrous high boiling liquid residue to replace the normal catalyst systems now used in preparing mono- and poly-glycol ethers virtually eliminates water in those reaction systems without adverse effect on product yield, distribution or purity and without forming undesirable glycol contaminants in the reaction product effluent, particularly in continuous processing systems. Thus, the inventive process further virtually eliminates the attendant problems of separating desired glycol ethers from glycol contaminants. The liquid anhydrous high boiling residue of the invention can be used in continuous processing systems by recycling it continuously for admixing with the alkylene oxide-alcohol feed streams.

DESCRIPTION OF THE DRAWING

The detailed description of our invention, which follows herein, will be further illustrated in connection with the attached drawing, which is a schematic flow sheet illustrating a preferred embodiment of the invention. In order to simplify the drawing, conventional details, such as valves, pumps, condensors, reboilers, surge tanks, flow and temperature control devices, and the like, have not been shown since the construction, operation and function thereof is known to those of ordinary skill in the chemical processing art.

DETAILED DESCRIPTION OF THE INVENTION

The anhydrous high boiling liquid residue of the present invention is preferably initially obtained by first mixing and reacting an alkylene oxide and an alcohol in the presence of about 0.05 to about 0.5 weight percent, based upon the weight of alcohol present, of sodium hydroxide or potassium hydroxide at a temperature of between about 90°–200°C. under a pressure of about 150–500 psig. The liquid reaction product effluent is then purified to remove excess unreacted alcohol and then the desired mono- and poly-glycol ethers are separated therefrom. The remaining liquid reaction product effluent residue, or bottoms, contains catalytically active alcoholates of sodium or potassium dissolved in higher glycol ethers and other unknowns. The residue is then concentrated by any conventional procedure, such as by flash distillation or wiped film evaporation removing about 80 to about 88 weight percent lower boiling materials to provide the anhydrous high boiling liquid residue. More particularly, the glycol ether bottoms residue is concentrated sufficiently to provide an anhydrous residue containing a sodium or potassium hydroxide level of at least 9 weight percent, and preferably about 10 to 30 weight percent, based upon the weight of the anhydrous residue, and depending upon the initial alkali metal or alkaline earth metal hydroxide catalyst employed.

It will be readily understood by those skilled in the art that the inventive anhydrous high boiling residue can be obtained by initially utilizing any conventional glycol ether process catalyst containing alkali or alkaline earth metal cations. However, we prefer to employ those wherein sodium or potassium hydroxide was utilized.

As mentioned hereinbefore, it is common practice in the industry to subject the glycol ether reaction product effluent to a plurality of purification and/or separation steps, such as by passing the effluent through a plurality of fractional distillation towers to remove excess unreacted alcohol and to separate the desired mono- and/or poly-glycol ethers in substantially pure form. As known, purification and separation conditions can be readily adjusted for the recovery of materials which meet desired specifications. In accordance with the present invention, the liquid reaction product effluent residue, or bottoms, from any purification or separation step, including the initial non-purified reaction product effluent, can be concentrated as described hereinabove to provide the catalytically active anhydrous high boiling liquid residue of the invention. Excess unreacted alcohol, glycol ethers, and other by-products are readily removed during the concentration. However, we prefer to utilize the glycol ether bottoms obtained from the last purification and/or separation step as the residue starting material.

The anhydrous high boiling liquid residue catalyst is employed in the same amounts as normal catalyst systems which usually ranges between about 0.05 to about 0.5 weight percent alkali or alkaline earth metal present, basis the alcohol reactant. The particular amount of alkali or alkaline earth metal present in a given anhydrous residue can be readily determined by well-known analytical procedures. Thus, one having skill in the relevant art can easily calculate the volumetric amount or weight percent of liquid residue catalyst required for a given process run with substantially no experimentation.

The anhydrous high boiling liquid residue catalyst can be used as a replacement or additive for normal catalyst systems in either conventional batch or continuous processing systems. It is particularly adaptable to continuous processing systems whereby its use provides an improvement in such systems as shown in the attached drawing.

Referring now to the drawing, in a continuous process for the preparation of mono- and poly-glycol ethers, flowing feedstock streams of an alcohol, catalyst, and an alkylene oxide are fed to a continuous reactor 10 at desired feed rates to provide the above-described reactant molor ratios and catalyst amounts. In the reactor 10, the reactants are heated in the presence of the normal catalyst material to a temperature of from about 50° to about 350°C. under a pressure of about 30 to about 3,000 psig. Upon completion of the reaction the crude reaction product effluents are fed through line 12 to a stripping still 14 which is operated under known temperature and pressure conditions to remove excess unreacted alcohol. This excess unreacted alcohol is taken overhead from the stripping still 14 through line 16 and is recycled back to the alcohol feedstock stream for reuse. The liquid bottoms or residue from the stripping still 14 is passed to line 18 and fed to a first refining still 20, such as a conventional distillation tower. The refining still 20 is operated under known conditions for taking desired mono- or poly-glycol ether specification product overhead. Usually, the refining still 20 is operated under known conditions to take lower glycol ethers overhead, e.g., ethlyene glycol monoethylether where the alcohol reactant is ethanol. The liquid bottoms or effluent from refining still 20 is then passed through line 22 to a second refining still 24 which is operated under known operating conditions for taking other desired mono- or poly-glycol ethers overhead, e.g., diethylene glycol monoethylether where ethanol is employed. As known in the art, refining stills 20 and 24 can be operated under selected operating conditions to take any desired mono- and poly-glycol ether products overhead in any desired admixture in as much as the boiling point of such materials are well known.

In accordance with the improved process of the present invention, the liquid reaction product effluent residue from the refining still 24 is passed through line 26 to a flash distillation still or wiped film evaporator 28 which is operated under conditions sufficient to take about 80 to about 88 weight percent of the residue overhead. The bottoms or residue obtained from the flash still 28 is the inventive anhydrous high boiling liquid residue having a caustic content of at least about 9 weight percent, preferably about 10 to about 30 weight percent, as described hereinabove. This concentrated anhydrous high boiling liquid residue can then be recycled through line 30 and fed to the reactor 10 for use as the catalyst for the alkylene oxide-alcohol reaction.

After the above-described continuous system has been in operation for a sufficient period of time to provide a sufficient amount of the concentrated anhydrous high boiling liquid residue for use in the above-described amounts as the catalyst for the alcohol-alkylene oxide reaction, the normal catalyst system feed stream, identified as catalyst in the drawing, can be cut off. The process can be continuously operated with recycling of the anhydrous high boiling liquid residue until it becomes too viscous to handle. When this occurs, the residues from the refining still 24 are discarded and the normal catalyst system restarted until a sufficient amount of the above-described anhydrous high boiling liquid residue is prepared and collected.

The anhydrous high boiling liquid residue containing catalytically active alcoholates of alkali or alkaline earth metals can be utilized as the catalyst in the reaction of any alkylene oxide and any alcohol, including higher molecular weight alcohols, polyhydric alcohols, and other compounds containing at least one hydroxyl group. The inventive anhydrous residue is particularly useful as a catalyst in reactions between an alkylene oxide containing two to four carbon atoms and saturated aliphatic monohydric alcohols having from one to four carbon atoms. Examples of such alkylene oxides include ethylene oxide, propylene oxide, and butylene oxide. Examples of such alcohols include methanol, ethanol, n-propanol, isopropanol, n-butanol, and t-butanol. Preferred alcohols then are saturated aliphatic monohydric alcohols having from 1 to 4 cabon atoms. Mixtures of alcohols can also be used. Moreover, the anhydrous high boiling liquid residue obtained from the reaction of a certain alkylene oxide and a certain alcohol can be employed as the catalyst for the reaction between other alkylene oxides and alcohols. For example, the concentrated anhydrous liquid residue obtained from the reaction of ethylene oxide and ethanol in the presence of sodium or potassium hydroxide catalyst can be employed as the catalyst in the reaction between ethylene oxide and n-butanol.

The following examples are for purposes of illustration of our invention only and are not to be limiting thereof. In the examples, a commercial continuous reactor system for the production of glycol ethers was employed. The reactor system included a continuous pressurized reactor, an alcohol stripping distillation tower and first and second product refining distillation towers connected by appropriate conduits and pumping apparatus. The system was also equipped with a flash distillation tower connected to the product refining towers and, through recycling means, to the reactor. Thus, the reactor system could be operated as desired to remove, concentrate and recycle the bottoms residue from either refining distillation tower back to the reactor or to bypass the flash distillation tower and recycling means.

EXAMPLE I

In a commercial continuous glycol ether unit equipped as described above, feed streams of methanol, concentrated aqueous caustic solution and ethylene oxide were pumped into a common feed line where they were mixed before entering the reactor. The mole ratio of methanol:ethylene oxide was about 2.9:1.0 while the catalyst solution was fed at a rate of about 0.1 weight percent caustic, basis the alcohol stream. The reactor was operated at about 160°C. and pressurized to about 220 psig. The reactor effluent was passed through the series of three distillation towers. Excess unreacted alcohol was taken overhead from the first stripping distillation tower while specification glycol ether product was taken overhead from the second and last distillation tower referred to as first and second refining towers. A sample of ethylene glycol monomethylether bottoms, taken from the first refining tower, was flash distilled at 5–6 mm. Hg vacuum and about 100° to 130°C., taking 88% as overhead. The flashed residue contained 9.2 weight percent caustic. Employing the same apparatus and process conditions described above, a second run was conducted utilizing ethyl alcohol and ethylene oxide feed streams in a mole ratio of ethanol:ethylene oxide of about 3:1 while the caustic catalyst was fed at a rate of about 0.15 weight percent caustic, basis the alcohol stream. A sample of diethylene glycol monoethyl ether bottoms, taken from the second (last) refining tower was passed through the flash distillation unit and flash distilled at 5–6 mm. Hg and about 100° to 130°C., taking 83% as overhead. The flashed residue contained 9.0 weight percent caustic.

Two runs were then conducted in the same apparatus under the same processing conditions utilizing feed streams of methanol, ethylene oxide and the flashed residue samples prepared above as catalysts in replacement of the normal concentrated caustic solution catalyst at the same weight percent caustic, basis alcohol stream. For each run the feed ratios of methanol and ethylene oxide were maintained to provide a mole ratio of about 2.9:1 methanol:ethylene oxide. Reactor conditions were also maintained for both runs. Samples of the crude reactor effluent from each run were taken and analyzed for product distribution. The analytical results are set forth in the following Table 1.

Table 1

| Distribution | Run 1* | Run 2** | Theory |
|---|---|---|---|
| Methanol,wt.% | 47.9 | 47.5 | 49.1 |
| Ethylene Glycol Monomethylether,wt.% | 38.4 | 38.0 | 38.9 |
| Diethylene Glycol Monomethylether,wt.% | 11.7 | 12.0 | 10.2 |
| Triethylene Glycol Monomethylether,wt.% | 2.2 | 2.4 | 1.6 |

*Run 1, flashed ethylene glycol monomethylether bottoms.
**Run 2, flashed diethylene glycol monoethylether bottoms.

As illustrated in the foregoing data, the flashed ethylene glycol monoether bottoms residue can be utilized as the catalyst in replacement of normal catalyst systems in the production of glycol ethers without any adverse effect on product yield or distribution.

EXAMPLE II

Employing the commercial continuous processing apparatus and process conditions described in Example I, two runs were conducted utilizing a feed stream of n-butanol and ethylene oxide in a mole ratio of about 4.0:1 alcohol:oxide. In the first run, a normal catalyst system of sodium hydroxide was used as the catalyst, while in the second run, the flashed ethylene glycol monomethylether bottoms residue prepared in Example I was used as the catalyst. In both runs the catalysts were fed at rates of about 0.1 weight percent caustic, basis the alcohol stream. Samples from the crude reactor effluent of both runs were taken and analyzed for product yield and distribution. The analytical results are set forth in the following Table 2.

Table 2

| Distribution | Run 1* | Run 2** | Theory |
|---|---|---|---|
| N-butanol, wt.% | 71.6 | 73.0 | 71.2 |
| Ethylene Glycol Mono-butylether,wt.% | 18.4 | 17.9 | 17.8 |
| Diethylene Glycol Mono-butylether,wt.% | 6.5 | 5.9 | 8.1 |
| Triethylene Glycol Mono-butylether,wt.% | 2.4 | 2.0 | 2.4 |
| Tetraethylene Glycol Mono-butylether,wt.% | 0.9 | 0.7 | 0.5 |

*NaOH catalyst used.
**Flashed ethylene glycol monomethylether bottoms catalyst used.

As shown in Table 2, the utilization of flashed glycol ether bottoms residue as a catalyst provides product yields and distributions substantially comparable to the utilization of a conventional catalyst system, such as Run No. 1, and are comparable to the theoretical distribution.

EXAMPLE III

Employing the commercial continuous processing apparatus and the process conditions described in Example I, a run was conducted utilizing a reactant feed stream mixture of methanol, ethylene oxide and concentrated aqueous caustic solution as catalyst in a mole ratio of methanol:oxide of about 3:1 while the catalyst feed rate was about 0.15 weight percent caustic, basis the alcohol stream. A sample of ethylene glycol monomethylether bottoms, taken from the first refining distillation tower, was passed through the flash distillation unit and flash distilled at 5–7 mm. Hg and about 100° to 130°C., taking 88% as overhead. The flashed concentrated residue contained 15 weight percent caustic. Two runs were then conducted utilizing the same apparatus and process conditions and reactant feed streams of ethyl alcohol and ethylene oxide in a mole ratio of about 1:1 alcohol:oxide. In the first run, a feed stream of potassium hydroxide was used as the catalyst, while in the second run, a stream of the above flashed ethylene glycol monomethylether bottoms was used as the catalyst. Samples from the crude reactor effluent of both runs were taken and analyzed for ethylene glycol content. The analytical results are in Table 3.

Table 3

| Distribution | Run 1* | Run 2** |
|---|---|---|
| Ethylene Glycol,wt.% | 0.12 | 0.004 |

*KOH catalyst used.
**Flashed ethylene glycol monomethylether bottoms catalyst used.

As shown in Table 3, the utilization of flashed glycol ether bottoms residue as a catalyst substantially reduces ethylene glycol formation. This corresponds to a reduction of the ethylene glycol content observed in the purified diethylene glycol monoethyl product overhead which was found to be 0.6 weight percent for Run No. 1 above and 0.2 weight percent for Run No. 2.

Obviously, many modifications and variations of the invention as hereinbefore set forth may be made without departing from the spirit and scope thereof, and, therefore, only such limitations should be imposed as are indicated in the following claims.

We claim:

1. In the method for the preparation of mono- and poly-glycol ethers comprising the steps of mixing and catalytically reacting an alkylene oxide containing 2 to 4 carbon atoms and an alcohol comprising a saturated aliphatic monohydric alcohol having from 1 to 4 carbon atoms in the presence of a catalyst containing alkali or alkaline earth cations at a temperature within the range of about 50° to about 350°C. under a pressure of about 30 to about 3,000 psig and then separating the desired mono- and poly-glycol ethers from the liquid reaction product effluent, the improvement comprising:

employing as said catalyst an anhydrous high boiling liquid residue containing catalytically active alcoholates of alkali or alkaline earth metals prepared in said process for the production of said desired mono- and poly-glycol ethers by concentrating the liquid residue of said reaction product effluent after said desired mono- and poly-glycol ethers have been separated therefrom.

2. The method of claim 1 wherein said anhydrous high boiling liquid residue is prepared by concentrating said reaction product effluent liquid residue to provide at least about 9 weight percent alkali or alkaline earth metal concentration, based on the weight of said anhydrous high boiling liquid residue.

3. The method of claim 2 wherein said reaction product effluent liquid residue is concentrated by heating at about 100° to about 130°C. under about 5 to 6 mm. Hg vacuum.

4. The method of claim 2 wherein about 80 to about 88 weight percent of said reaction product effluent liquid residue is removed therefrom.

5. The method of claim 1 wherein said alkali or alkaline earth cations are selected from the group consisting of sodium, potassium and mixtures thereof.

6. In the continuous process for the preparation of mono- and poly-glycol ethers comprising the steps of mixing flowing streams of an alkylene oxide containing 2 to 4 carbon atoms, an alcohol comprising a saturated aliphatic monohydric alcohol having from 1 to 4 carbon atoms and a catalyst containing alkali or alkaline earth cations, heating the admixture to about 50° to about 350°C. under a pressure of about 30 to about 3,000 psig until a crude reaction product effluent stream is formed, and passing the crude product effluent stream through a plurality of distillation units operated under conditions whereby excess unreacted alcohol and desired mono- and poly-glycol ethers are separated therefrom, the improvement comprising:

concentrating the crude reaction product effluent residue remaining after excess unreacted alcohol and desired mono- and poly-glycol ethers have been separated to provide an anhydrous high boiling liquid residue containing catalytically active alcoholates of alkali or alkaline earth cations, said crude reaction product effluent residue being concentrated in an amount sufficient to provide at least 9 weight percent alkali or alkaline earth metal concentration, based upon the weight of said anhydrous high boiling liquid residue; and recycling said anhydrous high boiling liquid residue to the flowing streams of ethylene oxide and alcohol whereby said residue is diluted therewith and used as said catalyst stream.

7. The process of claim 6 wherein about 80 to about 88 weight percent of said crude reaction product effluent residue is removed therefrom during said concentration.

8. The process of claim 6 wherein said alkali or alkaline earth cations are selected from the group consisting of sodium, potassium and mixtures thereof.

* * * * *